United States Patent
Pauley et al.

(10) Patent No.: US 6,512,146 B2
(45) Date of Patent: Jan. 28, 2003

(54) PROCESS FOR PREPARING A DIALKYL ACETAL OF A $C_8$ TO $C_{30}$ ALDEHYDE

(75) Inventors: Edward P. Pauley, Jesup, IA (US); Katherine Sue Neighbor, Alburnett, IA (US)

(73) Assignee: Penford Corporation, Bellevue, WA (US)

( * ) Notice: Subject to any disclaimer, the term of this patent is extended or adjusted under 35 U.S.C. 154(b) by 223 days.

(21) Appl. No.: 09/742,865

(22) Filed: Dec. 20, 2000

(65) Prior Publication Data

US 2001/0015267 A1 Aug. 23, 2001

Related U.S. Application Data

(62) Division of application No. 09/300,160, filed on Apr. 27, 1999, now Pat. No. 6,165,321.
(60) Provisional application No. 60/083,314, filed on Apr. 28, 1998.

(51) Int. Cl.⁷ ........................ C07C 43/30; C07C 43/11; C07C 43/18
(52) U.S. Cl. ........................ 568/594; 568/618; 568/619; 568/620
(58) Field of Search ........................ 568/594, 618, 568/619, 620

(56) References Cited

U.S. PATENT DOCUMENTS

| | | | |
|---|---|---|---|
| 3,080,281 A | 3/1963 | Fischer | 162/158 |
| 3,524,796 A | 8/1970 | Yui et al. | 162/158 |
| 3,957,574 A | 5/1976 | Anderson | 162/167 |
| 4,123,403 A | 10/1978 | Warner et al. | 260/29.2 EP |
| 4,657,946 A | 4/1987 | Rende et al. | 523/402 |
| 4,983,748 A | 1/1991 | Tsai et al. | 549/551 |
| 5,380,403 A | 1/1995 | Robeson et al. | 162/147 |
| 5,665,811 A | 9/1997 | Takeda et al. | 524/487 |

OTHER PUBLICATIONS

Arnson et al., "Internal Sizing With Stearic Acid," in *The Sizing of Paper*, Second Edition, Reynolds, W.F. (Ed.), pp. 79–87 (1989).
Dumas, D.H. "An Overview of Cellulose Reactive Sizes," TAPPI Sizing Seminar (Savannah) TAPPI Seminar Notes: 85–92 (Nov. 16–18, 1983).
Gupta, M.K., "A Novel Approach in Aquapel Sizing of Paper and Board," TAPPI Papermakers Conference 1979 TPCPDY Sep. 29, 1994, pp. 97–100.
Mahadevan, V., "Reactions of Fatty Aldehydes With–Fatty Alcohols: Formation of Acetals, Hemiacetals and Alk–1–enyl Alkyl Ethers," *Lipids, vol. 5 (No. 6)*:563–565 (1969).
Mar., *Advance Organic Chemistry*, 4$^{th}$ ed; John Wiley & Sons, New York, 1992, p. 889 and 1193–1194.

*Primary Examiner*—Johann Richter
*Assistant Examiner*—Sikarl A. Witherspoon
(74) *Attorney, Agent, or Firm*—Marshall, Gerstein & Borun

(57) ABSTRACT

Improved water resistant acetal sizing agents including 1,1-octadecoxyoctadecane are provided along with methods for their synthesis including methods in which $C_8$ to $C_{30}$ alkyl bromides are reacted with a polyol under basic conditions and those in which a $C_8$ to $C_{30}$ primary alcohol is reacted with an organic base in the presence of a suitable oxidizing agent under basic conditions.

10 Claims, No Drawings

PROCESS FOR PREPARING A DIALKYL ACETAL OF A $C_8$ TO $C_{30}$ ALDEHYDE

This is a divisional of U.S. application Ser. No. 09/300,160, filed Apr. 27, 1999 now U.S. Pat. No. 6,165,331 which claims the benefit of U.S. Provisional Patent Application Ser. No. 60/083,314, filed Apr. 28, 1998, the disclosure of which is hereby incorporated by reference.

BACKGROUND OF THE INVENTION

The present invention relates generally to sizing compounds, and particularly to compounds used to provide water resistance in the paper and textile industries. Specifically, the invention relates to long chain acetal compounds which are useful as sizing agents and novel methods for their production. A particularly preferred long chain, hydrocarbon-containing compound according to the invention is 1,1-octadecoxyoctadecane, the distearyl acetal of stearyl aldehyde. Further, the invention provides two novel and unexpected methods for synthesizing desired acetal compounds.

The paper industry has now largely converted to alkaline papermaking. The two main reasons for this change are the ability to use calcium carbonate ($CaCO_3$) and the ability to make a stronger and more permanent sheet. A major consequence of this change is that rosin cannot be used as the sizing agent in an alkaline system because rosin must be used with alum and the rosin/alum sizing system does not work at the higher pH range used to make alkane paper. (An exception to this are dispersed rosin sizes which have been used successfully at operating pH ranges as high as 6.5.) To make alkaline paper, the paper industry has turned to the synthetic reactive sizes, ASA (alkenyl succinic anhydride) and AKD (alkyl ketene dimer). These sizing agents work well in an alkaline environment by reacting with the fiber to form a covalent bond between the sizing compound and the hydroxyl groups on the fiber. The major problem with ASA and AKD is that they also react with water to form an insoluble non-sizing material.

ASA is the largest volume sizing agent now used by the paper industry and is the reaction product of an isomerized alpha olefin (with a chain length of C-16 to C-20) and maleic anhydride. The unsaturation and chain lengths of the starting olefin determine the melting point of the ASA (which is usually less than 9° C.) and it's sizing efficiency. Because ASA is an anhydride, it reacts rapidly with the hydroxyl groups on the fiber to form an ester linkage and with water to form a non-sizing hydrolyzate. The rapid reaction of ASA with fiber makes it the most used sizing agent where sizing is needed before the size press to control pickup, but the rapid reaction with water and the resultant non-sizing hydrolyzate, can cause problems for the paper maker such as press roll picking and machine deposits. ASA is not soluble in water and must be emulsified before use. Most ASA is emulsified using high shear emulsification equipment in the presence of a protective colloid such as starch or a synthetic polymer. Cationic starch such as cationic potato starch is most often used because of cost and the ready availability of wet end starch in most mills.

Because hydrolyzed ASA deposits are a major cause of runnability problems many limitations are imposed on its use. Thus, hydrolysis is minimized by using soft water, cooling the starch to room temperature before making down the emulsion and using the emulsion as soon as possible after it is made. If the emulsion must be stored for any length of time, the temperature must be kept low and the pH should be reduced to between 3 and 4. The ASA also must be added as close to the head box as possible to avoid prolonged contact with water. Finally, good first pass retention is critical so that ASA does not get into the white water system where it will hydrolyze and cause runnability problems. To achieve good first pass retention, retention aids should be used and strict attention must be paid to wet end chemistry. Stock pH and dryer settings are important to maximize size efficiency and minimize deposits.

AKD (alkyl ketene dimer) is the other commonly used cellulose reactive alkaline sizing agent but is less preferred than ASA because of its slow on-machine sizing development and higher cost. AKD is much less reactive than ASA, and can be emulsified by the manufacturer and shipped to the mill as a ready to use product. The lactone ring in AKD reacts with the hydroxyl groups on cellulose to form a β-keto ester on the cellulose fibers. Because the AKD is less reactive than ASA, much of the sizing occurs after the dryer section of the paper machine. In some cases, this may be insufficient to control wet end pick-up. AKD reacts with water to form the β-keto acid which rapidly decarboxylates to form the non-sizing, solid ketone. The reaction of AKD with water occurs very slowly at room temperature, such that emulsified AKD has a shelf life of at least a month. AKD sized sheets can also exhibit other problems such as size reversion, excessive sheet slipperiness and fugitive sizing. Like ASA, AKD should be added as close to the head box as possible.

Thus, while sizing agents currently used in the paper industry work well, they all exhibit some deficiencies. ASA's are very reactive, developing sizing within a few seconds to a few minutes. They are more efficient than rosin, and can be used with alum at pH values as low as 5. However, as ASA's are readily hydrolyzed, emulsions of these products are not very stable and require in-mill emulsification equipment for preparation. This process can be hard to control and the ASA, being very reactive with water as well as cellulose, can hydrolyze with water before it can react with the fiber leaving machine deposits. AKD's are less reactive than ASAs and have more stable emulsions, but are also less reactive with cellulose and may require several hours to develop sizing and usually require the concurrent use of a retention aid. Size reversion, fugitive sizing, and machine deposit problems are also encountered. Both AKD and ASA can make the sheet slippery, resulting in problems for users of reprographic paper. ASA and AKD can also contribute to "telescoping" of the paper reel which can lead to converting problems. Rosin is the lowest cost sizing product, but is much less efficient than ASA or AKD as a sizing agent on a per pound basis. Because of this low efficiency, relatively high dosage rates are required, especially when calcium carbonate is used as the filler. Rosin also does not work well at the higher pH range seen under ankaline papermaking conditions.

Of interest to the present invention is the art relating to the synthesis of acetals and ketals. Ordinarily the general preparative method for the synthesis of an acetal or ketal is the acid catalyzed addition of two moles of alcohol to one mole of aldehyde or ketone, with the formation of one mole of acetal or ketal and one mole of water. These reactions are only acid catalyzed and the products are formed by way of a hemiacetal or hemiketal intermediate. If the aldehyde is small, the reaction proceeds favorably. If the aldehyde is large, water must be removed as the material reacts. The reaction in neither direction is catalyzed by base, so most acetals and ketals are quite stable to bases, though they are easily hydrolyzed by acids (March, *Advance Organic Chemistry*, 4$^{th}$ ed; John Wiley & Sons, New York, 1992, p. 889).

Thus, for simple aldehydes, the overall equilibrium constant is favorable, and the acetal may be prepared simply by treating the aldehyde with two equivalents of alcohol and an acid catalyst. With ketones and larger aldehydes, the equilibrium constant for making the acetal or ketal is generally unfavorable. For most aldehydes, the alcohol can be used as the solvent to drive the equilibrium toward completion. For fatty acetals and ketals, the equilibrium constant is generally unfavorable and water must be removed during the reaction to drive the reaction to completion. Another method to prepare acetals and ketals, particularly fatty acetals and ketals is transacetalation of fatty aldehyde dimethyl acetals and fatty alcohols. (See for example, the disclosure of Mahadevan, Lipids, Vol. 5 (No. 6), pp. 563–565 (1969) which discloses a method for the synthesis of a C-14 acetal of fatty aldehydes and fatty alcohols by transacetalation between fatty aldehyde dimethyl acetals and fatty alcohols.) Acetals and ketals are normally stable to basic conditions, but are easily hydrolyzed back to the aldehyde or ketone and the alcohol under acidic conditions.

There is a need in alkaline papermaking for a sizing agent that works in an alkaline environment and does not hydrolyze in the presence of water. This sizing agent should have a low melting point and should develop some sizing before the size press. This new sizing agent should develop a predictable level of sizing and keep this sizing for the life of the sheet. The new product should be safe and made from readily available materials.

SUMMARY OF THE INVENTION

The present invention provides improved acetal sizing compositions and methods for their production. Specifically, the invention provides sizing methods and compositions comprising a dialkyl acetal of a $C_8$–$C_{30}$ aldehyde and an emulsifying agent. Preferred emulsifying agents include starches and synthetic polymers with cationic starch derivatives being particularly preferred starches. Preferred synthetic polymers include polyacrylamides, polyamides, paper makers alum, and of particular usefulness, the synthetic polymers described in U.S. Pat. No. 4,657,946. Other retention aids may be added to the size emulsion to improve retention of the size in the sheet.

According to a preferred aspect of the invention, the acetal is the dialkyl acetal, 1,1-octadecoxyoctadecane. The sizing composition may be used in a variety of applications including the sizing of substrates selected from the group consisting of paper and textiles and is particularly useful as a wet end size in paper manufacture.

The invention also provides new and improved methods for the synthesis of acetals under basic conditions. Specifically, the invention provides a first method of preparing a dialkyl acetal of a $C_8$ to $C_{30}$ aldehyde comprising the steps of: (a) reacting a carbohydrate with a base, in alcohol, to produce a caustic treated polyol; and (b) reacting a $C_8$ to $C_{30}$ alkyl bromide in the presence of the caustic treated polyol of step (a) and a suitable solvent to produce said dialkyl acetal. According to a preferred aspect of the invention the carbohydrate is preferably cellulose which can be in the form of cellulose fibers. The synthesis is carried out under basic conditions with the amount of base in the reaction mixture being controlled by the amount of caustic used to treat the fiber and the amount of said caustic treated fiber used in the reaction mixture. Accordingly, the base to fiber ratio can vary from 1:100 to 2:1 and the alkyl halide to caustic treated fiber ratio can vary from 1:50 to 50:1. Further, according to a preferred aspect of the invention the solvent of step (b) is dimethylsulfoxide (DMSO).

According to a second synthetic method of the invention a dialkyl acetal of a $C_8$ to $C_{30}$ aldehyde (preferably 1,1-octadecoxyoctadecane) is prepared by a method comprising the step of reacting a $C_8$ to $C_{30}$ primary alcohol with an organic base in the presence of a suitable oxidizing agent. Preferably, the primary alcohols are $C_8$ to $C_8$ Preferred bases for this reaction include: dimethylamine, ethylamine, diethylamine, n-propylamine, di-n-propylamine, tri-n-propylamine, isopropylamine, n-butylamine, sec-butylamine, tert-butylamine, cyclohexylamine, hexamethylenediamine, methylaniline, dimethylanline, o, m and p-anisidine, o, m and p-phenylenediamine, and o, m and p-toluidine. Diethylamine, triethylanine, n-propylamine, isopropylamine, n-butylamine, sec-butylanine and tert-butylamine are particularly preferred and triethylamine is most preferred. Various oxidizing agents may be used according to the invention with the preferred oxidizing agent being selected from the group consisting of n-chlorosuccinimide, n-bromosuccinimide, sodium hypochlorite and chlorine.

The novel sizing compound of this invention, when used as a paper sizing agent provides more consistent and predictable sizing, does not hydrolyze and leave machine deposits, provides sizing independent of pH and has unlimited shelf life. Moreover, the sizing agents of the invention provide improved waterproofing agents for paper, corrugated board including poultry boxes and milk carton stock, wood products including plywood and particle board, inorganic substrates such as wall board and textile products including those such as outdoor clothing and gear. Preferred fabrics which can be treated with the size so as to render them waterproof include but are not limited to cellulose-containing fabrics such as cotton and rayon. Moreover, the sizing compounds of the invention provide numerous improvements over other compounds currently available including improved durability due to better affinity of the compound to the fiber and greater potential for making the fabric both waterproof and breathable.

DETAILED DESCRIPTION

The present invention provides improved sizing compounds and new methods for their synthesis. Specifically, the invention provides highly efficient methods for producing long chain acetals under basic conditions without the requirement for water removal during the reaction. A particularly preferred compound for use as a size according to the invention is the acetal 1,1-octadecoxyoctadecane, $C_{54}H_{110}O_2$.

It is anticipated that most carbohydrates will work as the base support (caustic treated polyol) for the reaction of the alkyl halide to the acetal. Cellulose, in the form of wood fiber is the most convenient because it is insoluble in the solvent dimethylsulfoxide (DMSO) and it has the additional advantage of being an excellent carrier for the sizing agent in the wet end of the paper machine. While cellulose is currently preferred as the caustic treated polyol for these reactions, starch, particularly corn and potato starch, may also be used. It has been found, however, that while the reaction works well, the product of the caustic treated starch/alkyl halide reactions is a waxy material that is not as easy to use as the caustic treated cellulose/alkyl halide reaction product. A highly crosslinked starch, particularly if the starch is in the granular form and insoluble in DMSO, should provide a suitable substrate as the base support for these reactions. Using starch as the caustic treated polyol is very desirable because conventional sizing agents as well as those of the present invention, are preferably emulsified with starch before being used as a sizing agent in the paper making system.

The long chain acetals of the invention may be prepared by either of the two inventive methods described herein but may also be produced according to conventional methods known to the art. For example, while the acetal 1,1-octadecoxyoctadecane is preferably produced according to either of the two methods described in the following examples it may also be produced according to the general method described in Mahadevan, Lipids, Vol. 5 (No. 6), pp. 563–565 (1969) or other conventional methods.

The sizing agents of this invention are particularly well suited to the sizing of paper under alkaline conditions due to their unique ability to size the fiber without having to be covalently or ionically bonded to the fiber. The sizing agents of this invention are especially useful to the paper maker because they have a great affinity for carbohydrates, particularly cellulose and most especially wood fibers. The sizing agents of this invention will not hydrolyze in the presence of water or other paper making additives regardless of how long they are left in the system. Sizing material that is not retained on the first pass and gets into the white water system will retain its effectiveness as a size. This is also true for paper that contains the sizing agent that is repulped and added back into the paper making system. The sizing material of the invention which is retained on paper which is recycled in the mill (referred to as "broke") will not degrade and will retain its effectiveness as a size. While the sizing agents and compositions of the invention can be used in a variety of ways for paper sizing such as with a size press apparatus they have been found to be particularly useful as sizing agents for wet end sizing in the manufacture of paper.

Tests done with handsheets sized with this material have shown no fugitive sizing or size reversion, both of which are common with other sizing compounds, particularly AKD. The sizing agents of this invention, however, do share one characteristic in common with some other sizing agents. Full sizing is not obtained until about 4 hours after the sheets were made. While the degree of cure varies depending on the sample, in general the sheets show an increase in sizing from about 50 to 100%.

The examples of this invention disclose the use of these sizing agents with bleached hardwood and softwood pulps. These pulps are generally believed to be more difficult to size than mechanical pulp. It is expected that they can be used effectively to size any common wood pulp including but not limited to mechanical pulp (stone groundwood, refiner mechanical pulp, thermo-mechanical pulp), chemical-mechanical pulps (chemi-thermo-mechanical pulp, thermo-chemi-mechanical pulp and thermo-mechanical chemi pulp), semichemical pulps (neutral sulfite semichemical, high yield sulfite and high yield kraft pulp), and chemical pulps (kraft, sulfite and soda pulp). The sizing agents of this invention should also work well sizing other cellulose containing materials including but not limited to fiber, thread and fabric made from cotton, rayon, cellulose acetate, flax, jute, straw and hemp.

While examples disclosed have taught the use of straight chain, saturated hydrocarbons to make the novel sizing compounds of this invention, it will be apparent to those skilled in the art that other non-saturated and branched hydrocarbons will work equally as well. Specifically, compounds such as bromooctane, bromononane, bromodecane, bromoundecane, bromododecane, bromotetradecane, bromohexadecane, bromoicosane, 1-bromo-cis-4-octadecene, 1-bromo-cis,cis-9,12-octadecadiene, 1-bromo-4-hexadecyloctadecane, 1-bromo-4-tetradecyloctadecane, 1-bromo-4-hexadecylhexadecane and other saturated, unsaturated and branched long chain alkylbromides could be used in place of or in a mixture with the straight chain alkyl halides to lower the melting point and impart other specific properties to the sizing compound. In addition to bromine, other halogenated compounds could be used in these reactions. Chlorooctane, chlorononane, chlorodecane, chloroundecane, chlorododecane, chlorotetradecane, chlorohexadecane, chlorooctadecane, chloroicosane, 1-chloro-cis-4-octadecene, 1-chloro-cis,cis-9,12-octadecadien and other alkyl chlorides being the most common but also including alkyl iodides and alkyl fluorides. Likewise, octanol, nonanol, decanol, undecanol, dodecanol, tetradecanol, hexadecanol, icosanol, cis-9-octadecen-1-ol, cis,cis-9,12-octadecadiene-1-ol and other long chain saturated, unsaturated and branched alcohols could be used in place of the straight chain, saturated alcohols to impart or modify specific properties such as the melting point, of the sizing compounds. These are just a few examples of the many compounds that could be used in these reactions that would be apparent to others skilled in the art.

To use the objects of this invention, particularly as paper sizing compounds it is preferred that they be employed in combination with an emulsifier, preferably a cationic material, that also functions as a retention aid. Materials that are commonly used in the paper industry as emulsifying agents are cationic starch derivatives such as those produced from corn, potato, tapioca, and wheat starches and the like. These starches can be primary, secondary, tertiary or quarternary amine starches or other nitrogen containing starch derivatives. While starch is particularly preferred as an emulsifying agent for use in combination with the dialkyl acetal of $C_8$–$C_{30}$ aldehyde component in practice of the invention, other cationic materials may also be used. Other suitable emulsifying agents include synthetic polymers such as polyacrylamides, polyamides, and of particular usefulness, the synthetic polymers described in U.S. Pat. No. 4,657,946. In addition, components such as paper makers alum may also be used. While these materials, both starches and synthetic polymers are useful individually for the purposes of this invention, they may be combined one with another or with a surfactant to increase their effectiveness.

The sizing agent of the present invention is particularly suitable for uses in applications including paper, fabrics and non-wovens and has properties by which it operates as a one-way valve for water. Specifically, the sizing agents can be applied to substrates including but not limited to diapers, feminine products, incontinence products, umbrellas, raincoats, street clothes, cottons, camping supplies, knapsacks, hats, upholstery, lawn furniture, car seats and trim, work clothes, in tanneries, hospital, surgical and biomedical lab wear for the prevention of absorption of biological-aqueous fluids, tarps and covers. The sizing agents of this invention are further contemplated to be particularly useful for sizing items of clothing such as rain gear such that they will repel aqueous fluids and still remain breathable and comfortable. The novel sizing agents of this invention are also contemplated to be useful for impaling stain rise to aqueous fluids. According to the invention, the sizes may be applied to substrates according to conventional methods at concentrations which can be readily determined by those of skill in the art.

The following Examples are intended to illustrate practice of the preferred embodiments of the invention. Numerous additional embodiments and improvements are apparent upon consideration of the following Examples.

EXAMPLE 1

According to this example a first method for synthesizing long chain acetals is provided whereby the reaction of stearyl bromide (bromooctadecane) is carried out in DMSO (dimethyl sulfoxide) in the presence of caustic treated cellulose. As a first step, the fiber is caustic treated with KOH in ethanol. Specifically, a mixture of 91 g softwood and 227 g hardwood fiber was added to 50 pounds of tap water and beaten for 50 minutes in a Valley beater (Valley Iron Works, Appleton, Wis.). The fiber slurry was vacuum filtered through a large Buchner funnel to remove most of the water. About 100 g dry solids basis (ds basis) of the beaten fiber was then added to about 3.5 liters of ethanol (formula 3 A, denatured alcohol, EM Science, Gibbstown, N.J.). About 50 g of KOH was dissolved in 50 g of water and added to the fiber/alcohol slurry, and the entire mixture was heated, while stirring, to about 72° C. The mixture was held at 65–72° C. for about 15 minutes and allowed to cool to about 30° C. and vacuum filtered. The filter cake was broken up and spread out to air dry overnight to evaporate most of the alcohol.

According to the second step for producing long chain acetals, 47 g of the caustic treated cellulose was added to about 1800 g DMSO in a 2 liter Parr reactor (Parr Instrument Co., Moline, Ill.). To this mixture was added 75 g of stearyl bromide. The mixture was reacted, with stirring, at 85° C. for at least 24 hours (longer reaction times do not appear to hurt the reaction, but also did not seem to help significantly either). At the end of the reaction, the mixture was cooled and vacuum filtered through #42 Whatman filter paper. The filter cake was washed with ethanol and then reslurried in about 3 liters of ethanol and mixed well. The mixture was then vacuum filtered through #42 Whatman filter paper. The filter cake was washed and again reslurried in 3 liters of ethanol, mixed, vacuum filtered and washed with ethanol. The filter cake was then saved as an alcohol wet cake to prevent mold growth. The treated fiber at this point was composed of approximately 61% fiber and 39% long chain hydrocarbon. Based on HPLC analysis of the hydrocarbon portion, approximately 80% of the long chain hydrocarbon was the acetal, 1,1-octadecoxyoctadecane.

EXAMPLE 2

According to this example, the treated fiber of Example 1 was used as a sizing agent for malting paper (bandsheets). Handsheets were made using from 0.5 to 50% treated fiber (ds basis) based on ds pulp (from 10 to 1000 pounds per ton). Specifically, the alcohol wet cake was added to about 3 liters of warm water and mixed well. The mixture was then vacuum filtered through #42 Whatman filter paper. This wet cake was then emulsified in water and the emulsified material was added to the pulp slurry to make handsheets. Specifically, a sample of the reacted fiber wet cake was added to warm water and emulsified using a Cowles mixing blade and a laboratory mixer. For a 1% addition rate, 0.36 g (ds basis) treated fiber was added to about 440 ml tap water and heated to boiling for about 2 hours. The mixture was then mixed with a 1⅝ inch Cowles mixer at 1400 rpm for about 15 minutes. This emulsion was then added to 2059 g of 1.575 consistency pulp slurry (the pulp slurry was made up using 272 g bleached hardwood and 91 g bleached softwood pulp in 50 pounds of water and refined to a Williams freeness of 80 seconds). Handsheets were made using a Noble and Wood (file Nobel and Wood Machine Co., Hoosick Falls, N.Y.) handsheet machine. One ml of a 1:100 solution of Nalco 7607 (Nalco Chemical Company, One Nalco Center, Naperville, Ill.) in water was added as a retention aid to the deckle box of the handsheet machine for half the sheets. Typical handsheet bone dry weight was 3 g. Sizing was measured using a Hercules Size Tester (Hercules Inc., Wilmington, Del.), at 80% reflectance using 1:1 napthol green dye/2% formic acid as the test solution. HST on handsheets made with retention aid were 245 seconds average; HST on handsheets made without retention aid were 204 seconds average.

EXAMPLE 3

According to this example, the second method of the invention for producing a long chain acetal was carried out by reaction of stearyl alcohol (octadecanol) in DMSO in the presence of an oxidizing agent and an organic base. The oxidizing agent was either n-chlorosuccinimide or chlorine and the base was triethylamine. Specifically, 1000 g of n-chlorosuccinimide was dissolved in 1000 g of DMSO in a three liter round bottom flask with agitation. In a separate two liter glass beaker, 92 g of stearyl alcohol was emulsified in 1000 g of DMSO using an Ultra Turrax T-50 (Janke and Kunkel, Germany) with an emulsifying/chopping blade at about 6000 rpm for about 2 minutes. To the emulsified mixture of stearyl alcohol and DMSO was added 32 g of triethylamine. The emulsion was immediately added to the n-chlorosuccinimide/DMSO mixture with stirring. The mixture was heated with a heating mantle to 40° C. and held for 15 to 63 hours.

At the end of the reaction, about 4 liters of ethanol was added to the warm reaction mixture and mixed well. As the alcohol was added, material would begin to precipitate out of solution. The precipitated material was recovered by vacuum filtering (#42 Whatman filter paper). The filter cake was washed thoroughly with ethanol and placed in a small beaker on a hot plate. The material was heated gently to about 140 to 180° C. under nitrogen to drive off remaining ethanol and DMSO. The material was a white, crystalline solid with a melting point of 58–59° C. Total recovered material was about 33 g, for a yield of about 35%. The samples were analyzed by HPLC using two Altima C18 5 micron, 250×46 mm columns (Alltech Associates Inc., 2051 Waukegan Rd., Deerfield, Ill.) in series and an evaporative light scattering detector (ELSD) (Varex MKIII ELSD, Alltech Associates Inc., Deerfield, Ill.). Sample purity (of the 1,1-octadecoxyoctadecane) was about 90% by HPLC analysis.

EXAMPLE 4

According to this example, handsheets were produced using the 1,1-octadecoxyoctadecane product of Example 3 as the sizing agent. To test the handsheets, the sizing agent was first emulsified with starch and the emulsified material was added to a pulp slurry. Specifically, the 1,1-octadecoxyoctadecane sample was melted and added to a 4% solids (ds basis) cooked cationic corn starch paste (Pencat® 600, Penford Products Co., Cedar Rapids, Iowa) at a 3:1 ratio of starch to size. The hot starch/size mixture was emulsified using the Ultra Turrax T-50 with an emulsification blade set at 6000–8,000 rpm. The emulsion was added to 2080 g of 1.57% consistency pulp slurry (The pulp slurry was made using 272 g bleached hardwood pulp and 91 g bleached softwood pulp in 50 pounds of water.) The pulp was refined to a Williams freeness of 59 seconds. The sizing agent was added at a rate of 8 pounds per ton of ds fiber. Handsheets were made using a Nobel and Wood handsheet machine. One ml of a 1:100 solution of Nalco 7607 in water was added as a retention aid to the deckle box of the handsheet machine for half the sheets. Typical handsheet bone dry weight was 3 g. Sizing was measured using a Hercules Size Tester at 80% reflectance using 1:1 napthol green dye/2% formic acid as the test solution. HST on handsheets made with retention aid were 195 seconds average; HST on handsheets made without retention aid were 204 seconds average.

It is anticipated that numerous variations and modifications of the embodiments of the invention described above will occur to those of ordinary skill in the art when apprized of the teachings of the present specification. Accordingly, only such limitations as appear in the appended claims should be placed thereon.

What is claimed is:

1. A method of preparing a dialkyl acetal of a $C_8$ to $C_{30}$ aldehyde comprising the steps of: (a) reacting a carbohydrate with a base, in alcohol, to produce a caustic treated polyol; and (b) reacting a $C_8$ to $C_{30}$ alkyl bromide in the presence of the caustic treated polyol of step (a) and a suitable solvent to produce said distearyl acetal.

2. The method of claim 1 wherein said acetal is 1,1-octadecoxyoctadecane.

3. The method of claim 1 wherein said carbohydrate is cellulose.

4. The method of claim 1 wherein the solvent of step (b) is dimethylsulfoxide (DMSO).

5. A method of preparing a dialkyl acetal of a $C_8$ to $C_{30}$ aldehyde comprising the step of reacting a $C_8$ to $C_{30}$ primary alcohol with an organic base in the presence of a suitable oxidizing agent.

6. The method of claim 4 wherein said aldehyde and said primary alcohol are $C_8$ to $C_{24}$ aldehydes and alcohols.

7. The method of claim 4 wherein said acetal is 1,1-octadecxyoctadecane.

8. The method of claim 4 therein said organic base is an alkyl amine.

9. The method of claim 8 wherein said alkyl amine is triethylamine.

10. The method of claim 5 wherein said oxidizing agent is selected from the group consisting of n-chlorosuccinimide, n-bromosuccinimide, sodium hypochlorite and chlorine.

* * * * *

UNITED STATES PATENT AND TRADEMARK OFFICE
CERTIFICATE OF CORRECTION

PATENT NO. : 6,512,146 B2
DATED : January 28, 2003
INVENTOR(S) : Pauley et al.

It is certified that error appears in the above-identified patent and that said Letters Patent is hereby corrected as shown below:

Column 10,
Line 12, please delete "1, 1-octadecxyoctadecane" and insert
-- 1, 1-octadecoxyoctadecane -- in its place.
Line 13, after "The method of claim 4," please delete "therein" and insert
-- wherein -- in its place.

Signed and Sealed this

Sixteenth Day of September, 2003

JAMES E. ROGAN
*Director of the United States Patent and Trademark Office*